United States Patent [19]

Elsohly et al.

[11] Patent Number: 6,008,383

[45] Date of Patent: Dec. 28, 1999

[54] METHOD OF PREPARING DELTA-9-TETRAHYDROCANNABINOL ESTERS

[75] Inventors: Mahmoud A. Elsohly; Samir A. Ross; Shixia Feng, all of Oxford, Miss.

[73] Assignee: University of Mississippi, University, Miss.

[21] Appl. No.: 09/178,644

[22] Filed: Oct. 26, 1998

[51] Int. Cl.[6] .................................................. C07D 311/80
[52] U.S. Cl. ............................................................ 549/390
[58] Field of Search ................................................ 549/390

*Primary Examiner*—Amelia Owens
*Attorney, Agent, or Firm*—Graham & James LLP

[57] ABSTRACT

The present invention provides an economical and efficient process for converting delta-9-tetrahydrocannabinol to a variety of ester analogs. Delta-9-tetrahydrocannabinol is esterified by reaction with a carboxylic acid, an acid halide or an acid anhydride in the presence of a 4-aminopyridine either alone or in admixture with an organic amine such as a mono-, di-, or tri-alkyl amine.

17 Claims, No Drawings

METHOD OF PREPARING DELTA-9-TETRAHYDROCANNABINOL ESTERS

BACKGROUND OF THE INVENTION

Delta-9-tetrahydrocannabinol (THC, also known as Dronabinol) is the main biologically active component in the Cannabis plant which has been approved by the Food and Drug Administration (FDA) for the control of nausea and vomiting associated with chemotherapy and, more recently, for appetite stimulation of AIDS patients suffering from the wasting syndrome. The drug, however, shows other biological activities which lend themselves to possible therapeutic applications, such as in the treatment of glaucoma (1), migraine headaches (2,3), spasticity (4), anxiety (5), and as an analgesic (4). It is because of these-promising biological activities of THC that marijuana has been brought into a public debate relative its medicinal value. The balance between medicinal use of a drug and the abuse potential is a delicate balance. One of the main points brought by the medicinal marijuana proponents is the fact that the currently available soft gelatin capsule formulation is very expensive and lacks consistency in its effects. The latter point could be explained based on the fact that oral THC has erratic absorption from the gastrointestinal tract, is subject to the first-pass effect resulting in heavy metabolism with production of high levels of 11-OH-THC, and undesirable side effects. Another THC formulation which is currently under development is a pro-drug consisting of THC hemisuccinate formulated in a suppository base (6). This formulation appears to overcome the problems associated with the oral preparation and has been shown to produce consistent bioavailability in animal studies (7). Preliminary clinical investigations show promise for this formulation (8, 9, 10). It is anticipated that other THC formulations will be forthcoming in light of the current interest in the therapeutic activities of cannabis.

SUMMARY OF THE INVENTION

The present invention comprises an economic procedure and an efficient process for converting THC to its ester. The almost quantitative yield of conversion of THC to its ester distinguishes the present invention from the prior art.

THC can be esterified by reaction with an acid, an acid halide or an acid anhydride in the presence of a 4-aminopyridine either alone or in admixture with an organic amine such as, for example, an organic mono, di or trialkyl amine. The esterified THC can be purified by column chromatography and/or by HPLC.

DETAILED DESCRIPTION OF THE INVENTION

The present invention relates to providing an efficient and economic method for converting THC to the ester form.

A further aspect of the present invention relates to a process for the preparation of THC ester prodrug derivatives of the general formula:

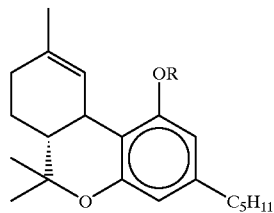

wherein R is an acyl group having a polar side chain, preferably R represents

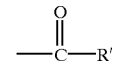

and R' is an alkyl containing a carboxyl or amino group and having from 2 to 10 carbon atoms. In a preferred embodiment of the invention R is the hemisuccinic acid ester. Another useful polar ester is the hemi-ester of malonic acid. It has been found that salts of the terminal carboxylic acid group of the ester, for example, the N-methyl glucamine salt as well as the sodium and potassium salts are also useful.

The compounds are disclosed and described in U.S. Pat. No. 4,933,368 and in U.S. Pat. No. 5,389,375. The disclosure of the '368 patent and the '1375 patent as well as the disclosures of all references which are recited in the present specification are expressly incorporated herein by reference thereto. These ester compounds are hydrolyzed in the blood stream releasing THC to provide a high degree of bioavailability of THC without regard to patient conditions and anomalies.

THC obtained by any means can be esterified by the reaction of THC with an organic acid, an organic acid halide or preferably organic acid anhydride in the presence of 4-amino-substituted pyridine alone or in admixture with an organic amine.

The 4-amino-substituted pyridines can be represented by the general formula:

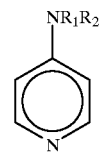

in which $R_1$ and $R_2$ are each independently H, optionally substituted lower alkyl, optionally substituted aryl or $R_1$ and $R_2$ can be taken together to form a carbocyclic or heterocyclic 5-or-6 membered ring. Illustrative substituted pyridines include, for ample, 4-dimethylaminopyridine and 4-pyrrolidinopyridine.

It will be understood by those skilled in the art that various modifications and substitutions may be made to the invention as described above without departing from the spirit and scope of the invention. Accordingly, it is understood that the present invention has been described by way of illustration and not limitation.

PREPARATION OF DELTA-9-TETRAHYDROCANNABINOL HEMISUCCINATE (THC-HS)

EXAMPLE NO. 1

To one gram of pure THC (purity about 95%) was added one gram succinic anhydride and 30 ml pyridine and the reaction mixture was refluxed for 24 hours. The reaction mixture was poured over 100 ml iced water and extracted with ether (30 ml×3). The ether extracts were combined, dried over anhydrous $Na_2SO_4$ and evaporated to dryness {TLC examination using silica gel plate, developing solvent: hexane-ether (80:20), visualizing agent: fast blue solution, showed that the yield was about 30–40%}. The residue was mixed with 5 g silica gel and 5 ml ether. The dried slurry was transferred on to the top of a silica gel column {40 g silica gel, dimensions: 3×50 cm}. Elution was carried out with hexane-ether mixtures in a manner of increasing polarities. The fractions eluted with hexane-ether (9:1) and ether were combined and evaporated to give 0.442 g of THC-HS (33% yield).

EXAMPLE NO. 2

To one gram of THC (95% purity) was added 0.5 g anhydrous $Na_2CO_3$, one gram succinic anhydride, and 20 ml dry benzene and the reaction mixture was refluxed for 24 hours. The reaction mixture was filtered and the filtrate was evaporated to dryness. The residue showed THC-HS content between 17–20% using HPLC analysis (C18 column using $MeOH:H_2O$: Acetic Acid at a ratio of 80:20:0.01).

EXAMPLE NO. 3

To one gram THC (purity 95%) was added 0.5 g succinic anhydride, 0.35 g 4-pyrrolidinopyridine and 20 ml benzene and the reaction mixture was kept at room temperature for 3 hours. TLC screening showed that the formation of THC-HS was about 20–30%. The reaction mixture was left overnight for 24 hours and TLC examined again (the % of THC-HS was about 30–50%). Then the reaction mixture was refluxed for 4 hours (% of THC-HS was 75.6%, HPLC analysis). The reaction mixture was refluxed for another 20 hours after the addition of 0.30 g of 4-pyrrolidinopyridine. HPLC analysis showed no increase in the % of THC-HS (about 75%).

EXAMPLE NO. 4

To one gram THC (95% purity) was added 0.5 g succinic anhydride, 0.4 g NaH, and 20 ml dry benzene and the reaction mixture was left at room temperature over weekend (72 hours). TLC examination showed that the % of THC-HS was small (about 20–30%). The reaction mixture was refluxed for about 24 hours, but the TLC examination showed no increase in the yield. HPLC analysis showed that the % of THC-HS was about 14.8%.

EXAMPLE NO. 5

To one gram THC (purity about 95%) was added 0.5 g succinic anhydride, 0.8 g 4-pyrrolidinopyridine and 30 ml benzene and the reaction mixture was refluxed for 24 hours, filtered and the filtrate was TLC examined. TLC showed that the % of THC-HS was about 50–60%. HPLC analysis showed that the % of THC-HS was 60%. The reaction mixture was worked up as follows: The benzene was evaporated and the residue was chromatographed on a silica gel column (50 g silica gel, 3×50 cm in dimensions). Fractions eluted with hexane-ether (9:1) and hexane-ether (85:15) were combined and evaporated to give 0.7 g of THC-HS (53% yield).

EXAMPLE NO. 6

To 1.1 g THC (purity 95%) was added 0.46 g succinic anhydride, 0.66 ml triethylamine, 78 mg 4-dimethylaminopyridine and 20 ml methylene chloride. The reaction mixture was left at room temperature for 3.5 hours. TLC examination showed that all the THC had been converted to THC-HS. The reaction was worked up as follows: the solvent was distilled off and the residue was purified on a silica gel column (50 g silica gel, 3×50 cm in dimensions). Fractions eluted with hexane-ether (9:1) and hexane-ether (8:2) were combined and evaporated to give 1.31 g of THC-HS, 95% purity using HPLC analysis. The total yield of THC-HS was 90.32%.

EXAMPLE NO. 7

To 0.5 g of pure THC (98% purity) was added 0.23 g succinic anhydride, 0.33 ml triethylamine, 39 mg 4-dimethylaminopyridine, and 10 ml methylene chloride. The reaction was left at room temperature in the dark for 24 hours. The solvent was distilled off and the residue was mixed with 1 g silica gel and 1 ml ether. The dried slurry was transferred on to the top of a silica gel column (7 g silica gel 60, dimensions: 1×50 cm). Fractions eluted with hexane-ether (9:1) and hexane-ether (85:15) were combined and evaporated to give 0.59 g of THC-HS (95.2% purity using HPLC analysis). The total yield of THC-HS was 88.5%.

EXAMPLE NO. 8

To 0.51 g pure THC (98% purity) was added 0.23 g succinic anhydride, 0.33 ml triethylamine, 40 mg 4-dimethylaminopyridine, and 10 ml methylene chloride. The reaction was left at room temperature in the dark for 24 hours. The reaction mixture was worked up as in Example No. 7 to give 0.61 g of THC-HS (96.5% purity using HPLC analysis). The total yield of THC-HS was 89.8%.

EXAMPLE NO. 9

To 2 g of THC (purity is about 92%) was added 0.92 g succinic anhydride, 1.4 ml triethylamine, 160 mg 4-dimethylaminopyridine, and 40 ml methylene chloride. The reaction was left at room temperature for 24 hours. The reaction mixture was then worked-up as in Example No. 6. Fractions eluted with hexane-ether (9:1) and hexane-ether (85.15) were combined and evaporated to give 2.24 g of THC-HS with 98.6% purity. The total yield of THC-HS was 85%.

EXAMPLE NO. 10

To 1 g of THC (purity is about 92%) was added 0.46 g succinic anhydride, 0.7 ml triethylamine, 79 mg 4-dimethylaminopyridine and 20 ml methylene chloride and the reaction mixture was kept at room temperature in dark for 24 hours. The solvent was distilled off and the residue was mixed with 1 g silica gel and 1 ml ether. The dried slurry was chromatographed on a silica gel column (10 g silica gel, dimensions: 1×50 cm ). Fractions eluted with hexane-ether (9:1) and hexane-ether (85:15) were combined and evaporated to give 1.17 g of THC-HS, (88.7% yield). The THC-HS residue was again rechromatographed on a silica gel column (10 g silica gel, dimensions 1×50 cm) to yield 1.03 g of pure THC-HS (98% purity).

EXAMPLE NO. 11

To 1 g of THC (92% purity) was added 0.46 g succinic anhydride, 0.7 ml triethylamine, 80 mg 4-dimethylaminopyridine and 20 ml methylene chloride and the reaction mixture was kept at room temperature in dark for 24 hours. The solvent was distilled off and the residue was dissolved in 10 ml hexane and transferred on to the top of a silica gel column [10 g silica gel, 230–400 mesh, lot G 42352, dimensions: 1×50 cm]. The column was eluted with hexane (100 ml), followed by hexane-ether (95:5)[100 ml], hexane ether (90:10)[100 ml] and hexane-ether (80:20)[300 ml]. The last fraction was evaporated to give 1.2 g of THC-HS (98% yield), purity was over 98% with HPLC analysis.

EXAMPLE NO. 12

To 50 mg of THC (purity is 98%) was added 25 mg succinic anhydride, 0.04 ml triethylamine and 2.5 ml methylene chloride and the reaction mixture was kept at room temperature in the dark for 24 hours. TLC examination (silica gel plate, developing system: Hexane-ether 80:20) showed that only about 30–40% of THC had been converted to THC-HS.

EXAMPLE NO. 13

To 50 mg of THC (purity is 98%) was added 25 mg succinic anhydride, 5 mg 4-dimethylaminopyridine and 2.5 ml methylene chloride and the reaction mixture was kept at room temperature in the dark for 24 hours. TLC examination (silica gel plate, development system: Hexane-ether 80:20) showed that a small amount of THC had been converted to THC-HS (25–30%).

REFERENCES

1. ElSohly, M. A.; Harland, E.; and Waller, C. W.; Cannabinoids in glaucoma II: The effect of different cannabinoids on the intraocular pressure of the rabbit; *Curr. Eye Res.*; 3(6):841–850, 1984.
2. El-Mallakh, R. S.; Marihuana and migraine, *Headache*, 27(3):442–443, 1987.
3. Volfe, Z.; Dvilansky, I. A., and Nathan, I.; Cannabinoids block release of serotonin from platelets induced by plasma from migraine patients; *Int. J. Clin Pharmacol. Res.*, 5(4):243–246, 1985.
4. Maurer, M; Henn, V.; Dirtrich, A.; and Hofmann, A.; Delta-9-tetrahydrocannabinol shows antispastic and analgesic effects in a single case double-blind trial; *Eur. Arch. Psychiatry Clin. Neurosci.*, 240(1):1–4, 1990.
5. McLendon, D. M., Harris, R. T.; Maule, W. F.; Suppression of the cardiac conditioned response by delta-9-tetrahydrocannabinol: A comparison with other drugs; *Psychopharmacology*, 50(2): 159–163, 1976.
6. ElSohly, M. A., Stanford, D. F.; Harland, E. C.; Hikal, A. H.; Walker, L. A.; Little, T. L., Jr.; Rider, J. N.; and Jones, A. B.; Rectal bioavailability of delta-9-tetrahydrocannabinol from the hemisuccinate ester in monkeys; *J. Pharm. Sci.*, 80(10):942–945, 1991.
7. ElSohly, M. A., Little, T. L., Jr.; Hikal, A.; Harland, E.; Stanford, D. F.; and Walker L. A.; Rectal bioavailability of delta-9-tetrahydrocannabinol from various esters; *Pharmacol., Biochem., Behav.*, 40:497–502, 1991.
8. Mattes, R. D.; Shaw, L. M.; Edling-Owens, J., Engleman, K.; and ElSohly, M. A.; Bypassing the first-pass effect for the therapeutic use of cannabinoids; *Pharm., Biochem., Behav.*, 44(3):745–747, 1991.
9. Mattes, R. D.; Engelman, K.; Shaw, L. M.; and ElSohly, M. A.; Bypassing the first-pass effect for the therapeutic use of cannabinoids, *Pharmacol., Biochem., Behav.*, 49(1):187–195, 1994.
10. Brenneisen, R.; Egli, A.; ElSohly, M. A.; Henn, V.; and Speiss, Y.; The effect of orally and rectally administered delta-9-tetrahydrocannabinol on spasticity: A pilot study with 2 patients; *Inter. J. Clin. Pharmacol. and Therapeutics*, 34(10):446–452, 1996.

We claim:

1. A process for the preparation of a compound of the formula:

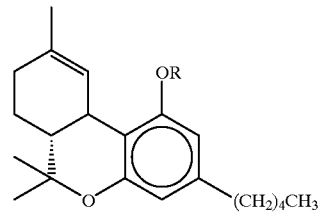

in which R represents an acyl group, said process comprising reacting delta-9-tetrahydrocannabinol with a carboxylic acid, acid halide or acid anhydride having R as the residue group in the presence of a 4-amino-substituted pyridine.

2. The process of claim 1, where the 4-amino-substituted pyridine is a compound of the formula

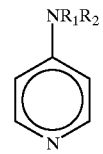

in which $R_1$, and $R_2$ are each independently H, optionally substituted lower alkyl, optionally substituted aryl or $R_1$ and $R_2$ can be taken together to form a carbocyclic or heterocyclic 5-or-6 membered ring.

3. The process of claim 1, further comprising carrying out the esterification with the additional presence of a further organic amine.

4. The process of claim 1, in which R is a group of the formula:

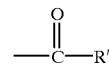

in which R' is an alkyl containing a carboxyl or an amino group.

5. The process of claim 1, wherein R is the hemiester of succinic acid.

6. The process of claim 1, wherein R is the hemiester of malonic acid.

7. The process of claim 1, wherein the 4-substituted pyridine is 4-pyrrolidinopyridine.

8. The process of claim 1, wherein the 4-substituted pyridine is a 4-diloweralkylaminopyridine.

9. The process of claim 1, wherein the 4-substituted pyridine is 4-dimethylaminopyridine.

10. The process of claim 3, wherein the organic amine is a mono-, di-, or tri-lower alkyl amine.

11. The process of claim 10, wherein the organic amine is triethylamine.

12. The process of claim 1 wherein R is the acyl residue of succinic acid, the acid anhydride is succinic anhydride and the base is a mixture of 4-dimethylamine pyridine and triethylamine.

13. The process of claim 1, wherein the delta-9-tetrahydrocannabinol is reacted with a carboxylic acid.

14. The process of claim 1, wherein the delta-9-tetrahydrocannabinol is reacted with an acid halide.

15. The process of claim 1, wherein the delta-9-tetrahydrocannabinol is reacted with an acid anhydride.

16. The process of claim 1, wherein R represents an acyl group having an alkyl side chain containing a polar group.

17. The process of claim 4, wherein R' is an alkyl containing between 2 to 10 carbon atoms.

* * * * *